United States Patent

Miyazaki

[11] Patent Number: 5,868,679
[45] Date of Patent: Feb. 9, 1999

[54] BLOOD-PRESSURE MONITOR APPARATUS

[75] Inventor: Makoto Miyazaki, Konan, Japan

[73] Assignee: Colin Corporation, Komaki, Japan

[21] Appl. No.: 749,213

[22] Filed: Nov. 14, 1996

[51] Int. Cl.⁶ .................................................. A61B 5/00
[52] U.S. Cl. ......................... 600/494; 600/495; 600/500
[58] Field of Search .................................. 600/485, 490, 600/493–6, 500

[56] References Cited

U.S. PATENT DOCUMENTS

| | | | |
|---|---|---|---|
| 4,699,152 | 10/1987 | Link | 600/494 |
| 4,718,427 | 1/1988 | Russell | 600/494 |
| 5,279,303 | 1/1994 | Kawamura et al. | 600/496 |
| 5,590,649 | 1/1997 | Caro et al. | 600/500 |

FOREIGN PATENT DOCUMENTS

| | | |
|---|---|---|
| A-60-241422 | 11/1985 | Japan . |
| A-61-103432 | 5/1986 | Japan . |

Primary Examiner—Robert L. Nasser
Attorney, Agent, or Firm—Oliff & Berridge, PLC

[57] ABSTRACT

A blood pressure monitor apparatus for monitoring a blood pressure of a living subject, by changing a pressing pressure of an inflatable cuff being wound around a body portion of a living subject, including a cuff-pressure regulating device which iteratively changes the pressure of the cuff within a predetermined range whose upper limit is lower than a mean blood pressure of the subject, a pulse-wave sensor which detects an amplitude of each of a plurality of heartbeat-synchronous pulses of a pulse wave which is produced in the cuff when the pressure of the cuff is changed within the predetermined range by the regulating device, a characteristic determining device for determining a characteristic value relating to an envelope of the pulse amplitudes detected by the pulse-wave sensor during each of the iterative cuff-pressure changes within the predetermined range, and a identifying device for identifying an abnormal decrease of the blood pressure of the subject based on the characteristic value determined by the characteristic determining device.

20 Claims, 9 Drawing Sheets

BLOOD-PRESSURE MONITOR APPARATUS

BACKGROUND OF THE INVENTION

1. Field of the Invention

The present invention relates to a blood-pressure monitor apparatus which monitors the blood pressure of a living subject.

2. Related Art Statement

The blood pressure of a living subject such as a patient may continuously be monitored by using an automatic blood-pressure (BP) measuring device including an inflatable cuff adapted to be wound around a body portion (e.g., upper arm) of the subject. In this case, the BP measuring device periodically carries out BP measuring operations at a regular interval of time. However, if this interval is shortened to improve the reliability of the BP monitoring, then the frequency of pressing of the cuff against the subject's body portion increases, thereby causing the subject to feel even serious discomfort.

In contrast, a different BP monitoring method is disclosed in Japanese Patent Applications laid open for inspection under Publication Nos. 61-103432 and 60-241422. In this method, an inflatable cuff is wound around a body portion of a living subject and is inflated to apply an appropriate pressing pressure to the body portion, and a pulse-wave sensor continuously detects heartbeat-synchronous pulses produced as pressure oscillations in the cuff. The disclosed BP monitor device continuously estimates the BP values of the subject based on the respective amplitudes of the continuous pulses.

However, in the above-described BP monitor device, the pressing pressure of the cuff cannot be decreased to sufficiently low levels to be able to reduce the physical and/or psychological load to the subject, because the changing of the pulse amplitudes at such low levels does not accurately correspond to the changing of the subject's blood pressure. A curve indicated at solid line in FIG. 35 represents the envelope of the pulse amplitudes which are obtained from the cuff as the cuff pressure $P_c$ is changed. If the blood pressure of the subject decreases from a normal level represented by the solid-line curve, the solid-line curve is changed into a curve indicated at one-dot chain line in the same graph. In the case where the pulse amplitudes are detected at a low cuff pressure $P_K$, the amount of changing of the pulse amplitudes is significantly smaller than that of the subject's blood pressure, thereby lowering the accuracy of monitoring of the prior BP monitor device.

SUMMARY OF THE INVENTION

It is therefore an object of the present invention to provide a blood-pressure monitor apparatus which monitors the blood pressure of a living subject with high accuracy and without causing the subject to feel discomfort.

The above object has been achieved by the present invention, which provides a blood pressure monitor apparatus for monitoring a blood pressure of a living subject, by changing a pressing pressure of an inflatable cuff being wound around a body portion of a living subject, comprising a cuff-pressure regulating device which iteratively changes the pressure of the cuff within a predetermined range whose upper limit is lower than a mean blood pressure of the subject; a pulse-wave sensor which detects an amplitude of each of a plurality of heartbeat-synchronous pulses of a pulse wave which is produced in the cuff when the pressure of the cuff is changed within the predetermined range by the regulating device; characteristic determining means for determining a characteristic value relating to an envelope of the pulse amplitudes detected by the pulse-wave sensor during each of the iterative cuff-pressure changes within the predetermined range; and identifying means for identifying an abnormal decrease of the blood pressure of the subject based on the characteristic value determined by the characteristic determining means.

In the blood pressure (BP) monitor apparatus constructed as described above, the blood pressure of a living subject is monitored by utilizing the finding that the slope of the envelope of pulse amplitudes detected while the cuff pressure is changed within a predetermined range under a mean BP value of the subject changes in response to a change of the blood pressure of the subject. Thus, the blood pressure of the subject is monitored with high accuracy. In addition, since the slope of the envelope is obtained by changing the cuff pressure within a low pressure range whose upper limit is lower than the mean BP value of the subject, the subject does not feel discomfort due to the pressing of the cuff.

In a preferred embodiment of the present invention, the characteristic determining means comprises area-using characteristic determining means for determining the characteristic value based on an area defined by the envelope of the pulse amplitudes and a base line connecting a plurality of cuff pressures corresponding to the pulse amplitudes, respectively. The area may be calculated by integration, or by approximation.

In another embodiment of the present invention, the area-using characteristic determining means comprises means for determining, as the characteristic value, a ratio of the area to the pulse amplitude corresponding to a lower limit of the predetermined range. Alternatively, the characteristic value may be determined as a ratio of the area to the pulse amplitude corresponding to an upper limit of the predetermined range.

In another embodiment of the present invention, the area-using characteristic determining means comprises means for determining, as the characteristic value, an area defined by the base line and an envelope of respective normalized values of the pulse amplitudes.

In another embodiment of the present invention, the characteristic determining means comprises amplitude-using characteristic determining means for determining the characteristic value based on at least two of the pulse amplitudes.

In another embodiment of the present invention, the amplitude-using characteristic determining means comprises means for determining, as the characteristic value, a ratio of the pulse amplitude corresponding to the upper limit of the predetermined range to the pulse amplitude corresponding to a lower limit of the predetermined range Alternatively, the characteristic value may be determined as a ratio of the pulse amplitude corresponding to a lower limit of the predetermined range to the pulse amplitude corresponding to the upper limit of the same range.

In another embodiment of the present invention, the amplitude-using characteristic determining means comprises means for determining, as the characteristic value, a difference between the pulse amplitude corresponding to the upper limit of the predetermined range and the pulse amplitude corresponding to a lower limit of the predetermined range.

In another embodiment of the present invention, the blood pressure monitor apparatus further comprises a blood pressure measuring device which automatically carries out, when the identifying means identifies the abnormal decrease of the blood pressure of the subject, a blood pressure measurement on the subject according to a series of predetermined steps. In this embodiment, since the blood pressure measuring device automatically measures a BP value or values of a patient at the time when an abnormal BP decrease of the patient is identified, a doctor or a nurse can quickly read the BP values of the patient and do appropriate treatments on the subject.

In another embodiment of the present invention, the blood pressure monitor apparatus further comprises a pulse-rate sensor which detects a pulse rate of the subject when the pressure of the cuff is changed within the predetermined range by the regulating device.

In another embodiment of the present invention, the pulse-rate sensor comprises pulse-rate determining means for determining the pulse rate based on at least two pulses of the heartbeat-synchronous pulses of the pulse wave detected by the pulse-wave sensor from the cuff when the pressure of the cuff is changed within the predetermined range by the regulating device.

In another embodiment of the present invention, the blood pressure monitor apparatus further comprises pulse-rate-change determining means for determining a change of a current pulse-rate value detected by the pulse-rate sensor, from at least one prior pulse-rate value detected by the pulse-rate sensor before the current pulse-rate value is detected.

In another embodiment of the present invention, the pulse-rate-change determining means comprises means for determining the change of the current pulse-rate value from a moving average of a plurality of prior pulse-rate values detected by the pulse-rate sensor before the current pulse-rate value is detected. In this embodiment, the change of pulse rate is prevented from being adversely influenced by noise, and accordingly the accuracy of determination of the pulse-rate change is improved.

In another embodiment of the present invention, the blood pressure monitor apparatus further comprises reference-value determining means for determining a reference value, $R^*$, based on the pulse-rate change, $\Delta PR$, determined by the pulse-rate-change determining means, according to a following predetermined expression:

$$R^* = k_1 \times \Delta PR + k_2$$

where $k_1$ and $k_2$ are a first and a second constant, respectively,
wherein the identifying means identifies the abnormal decrease of the blood pressure of the subject when the characteristic value determined by the characteristic determining means is greater than the reference value $R^*$. In the case where the blood pressure of a patient abnormally decreases because of falling in shock, the envelope of pulse amplitudes detected from the patient in shock becomes flat or level. In this case, it is not easy to identify the shock of the patient based on only the slope of the pulse amplitudes with respect to the cuff pressure. In the present embodiment, however, the reference value $R^*$ is determined depending upon the pulse-rate change $\Delta PR$ that decreases as the blood pressure of the patient decreases. Thus, the blood pressure of the patient, i.e., the characteristic value that increases as the blood pressure of the patient decreases is monitored in association with the pulse rate of the patient, i.e., reference value $R^*$. Accordingly, the present BP monitor can immediately identify, with high accuracy, that the patient has fallen in shock.

In another embodiment of the present invention, the blood pressure monitor apparatus further comprises a memory which stores data indicative of the predetermined expression.

In another embodiment of the present invention, the cuff-pressure regulating device comprises means for changing the pressure of the cuff to a predetermined first hold value equal to a lower limit of the predetermined range and holding the cuff pressure at the first hold value and changing the cuff pressure to a predetermined second hold value higher than the first hold value and equal to the upper limit of the predetermined range and holding the cuff pressure at the second hold value, and the characteristic determining means determines the characteristic value based on the pulse amplitude detected by the pulse-wave sensor when the cuff pressure is held at the first hold value and the pulse amplitude detected by the pulse-wave sensor when the cuff pressure is held at the second hold value. Since the pulses detected when the cuff pressure is held at the first and second hold values are free from distortion, the characteristic determining means determines, with high accuracy, the characteristic value based on the respective amplitudes of those pulses. Therefore, the blood pressure of the subject can be monitored with high accuracy.

In another embodiment of the present invention, the pulse-wave sensor comprises means for detecting an identical amplitude of two heartbeat-synchronous pulses of the pulse wave when the pressure of the cuff pressure is held at each of the first and second hold values, wherein the characteristic determining means determines the characteristic value based on the identical pulse amplitude detected by the pulse-wave sensor when the cuff pressure is held at the first hold value and the identical pulse amplitude detected by the pulse-wave sensor when the cuff pressure is held at the second hold value.

In another embodiment of the present invention, the blood pressure monitor apparatus further comprises a blood pressure measuring device which automatically carries out a blood pressure measurement on the subject at a predetermined period, wherein the cuff-pressure regulating device automatically changes the pressure of the cuff at a predetermined period which is shorter than the predetermined period of operation of the blood pressure measuring device.

In another embodiment of the present invention, the blood pressure monitor apparatus further comprises an output device which outputs information indicating that the identifying means identifies the abnormal decrease of the blood pressure of the subject.

In another embodiment of the present invention, the cuff-pressure regulating device comprises means for changing the pressure of the cuff within the predetermined range whose upper limit is lower than a diastolic blood pressure of the subject.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Figure 1:
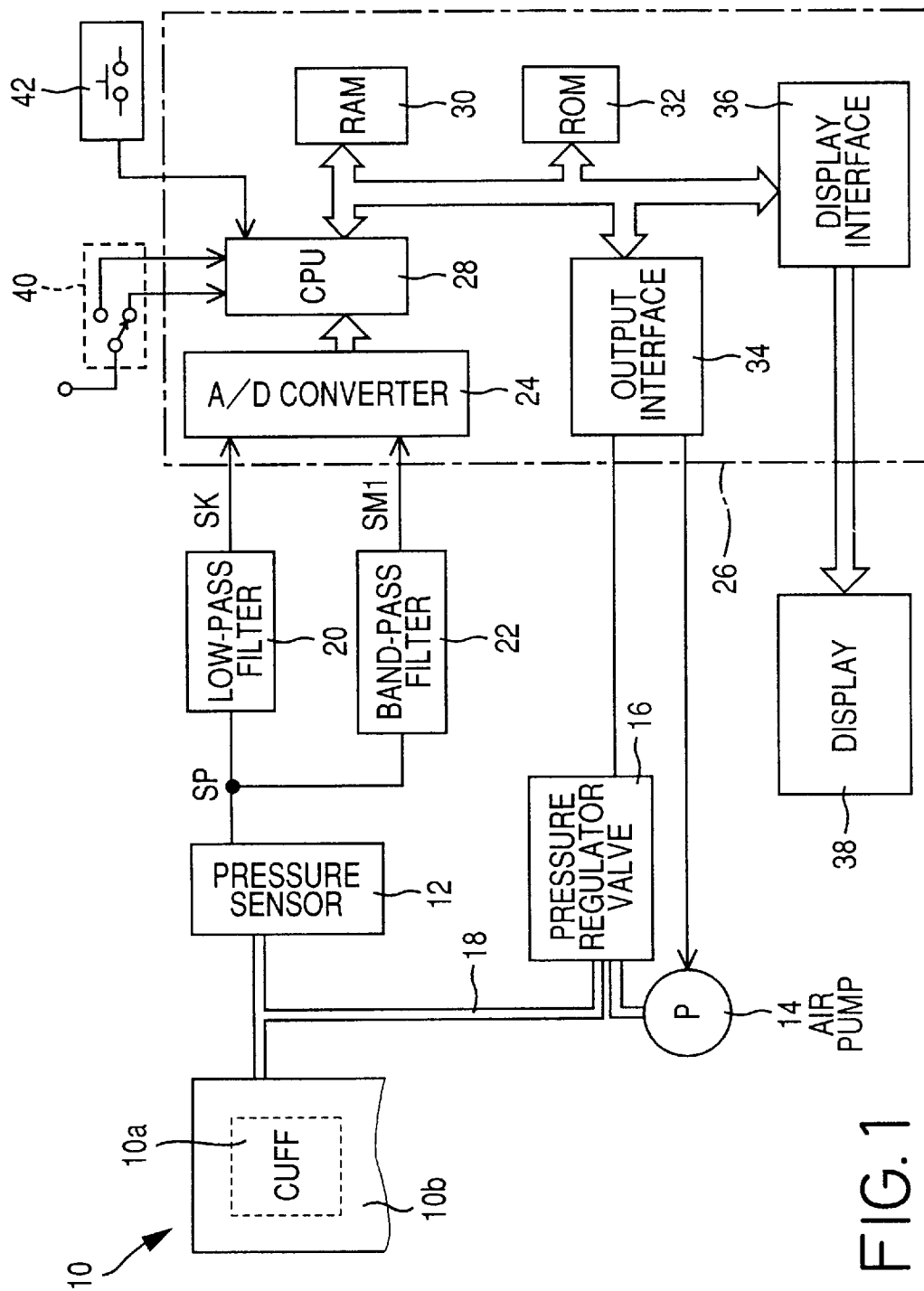
FIG. 1 is a diagrammatic view of a blood-pressure (BP) monitor apparatus embodying the present invention.

Referring to FIG. 1, there is shown a blood pressure monitor apparatus embodying the present invention (hereinafter, referred to as the "BP monitor").

In FIG. 1, reference numeral 10 designates an inflatable cuff 10 adapted to be wound around, e.g., an upper arm of a living subject, such as a patient, so as to press the arm. The cuff 10 includes an inflatable bag 10a formed of an elastic sheet such as a rubber sheet or a vinyl sheet. The inflatable bag 10a is accommodated in an arm belt 10b formed of a non-stretchable sheet. The bag 10a of the cuff 10 is connected to a pressure sensor 12, an air pump 14, and a pressure regulator valve 16 via air piping 18. The pressure regulator valve 16 controls the pressing pressure (i.e., air pressure) of the cuff 10 applied to the upper arm of the subject. Thus, the regulator valve 16 provides part of a cuff-pressure regulating device 54 (FIG. 2) which will be described later.

The pressure sensor 12 includes a semiconductor pressure-sensing element, detects the air pressure in the cuff 10, and supplies a pressure signal, SP, representative of the detected cuff pressure, to a low-pass filter 20 and a band-pass filter 22. The low-pass filter 20 permits only a direct-current component of the pressure signal SP to pass therethrough, thereby supplying a cuff-pressure signal, SK, representative of a cuff pressure (i.e., static pressure), $P_c$, to an analog-to-digital (A/D) converter 24. The low-pass filter provides part of a blood-pressure (BP) measuring device 52 (FIG. 2) which will be described later.

The band-pass filter 22 permits only a 1 to 10 Hz frequency-band component of the pressure signal SP to pass therethrough, thereby supplying, to the A/D converter 24, a pulse-wave signal, $SM_1$, representative of a pulse wave including heartbeat-synchronous pulses that are pressure oscillations or changes produced in the cuff 10 because of the pulsation of arterial vessels (e.g., brachial artery) running in the subject's arm. The band-pass filter 22 has a narrow frequency-band characteristic to extract, from the pressure signal SP, pulse amplitudes, i.e., pressure oscillations which are produced in the cuff 10 in synchronism with the subject's heartbeats while the cuff pressure $P_c$ is slowly changed (e.g., decreased) at the rate of, e.g., 2 to 3 mmHg/sec. Thus, the pulse-wave signal $SM_1$ is free from noise such as motion-induced artifact noise. The A/D converter 24 includes a multiplexer for concurrently dealing with the two input signals, SK and $SM_1$, by time sharing. The band-pass filter 22 provides part of a pulse-wave sensor 50 which will be described later.

The present BP monitor has a control device 26 which is provided by a microcomputer including a central processing unit (CPU) 28, a random access memory (RAM) 30, a read only memory (ROM) 32, an output interface 34, and a display interface 36. The CPU 28 processes the signals SK, $SM_1$ received from the A/D converter 24, by utilizing a temporary-storage function of the RAM 30, according to a control program pre-stored in the ROM 32. In addition, the CPU 28 drives and controls the air pump 14 and the pressure regulator valve 16 via the output interface 34, and drives and controls a display 38 via the display interface 36. The display 38 includes a display panel for displaying an image which consists of a multiplicity of picture elements and represents numerals and/or waveforms, and a printer for recording the image with an ink on a recording sheet. In the present embodiment, the display 38 corresponds to an output device 68 (FIG. 2).

A mode-selection switch 40 is operable for switching the BP monitor between a single-measurement mode and a BP-monitor mode. The mode switch 40 supplies, to the CPU 28, a mode signal representing a selected mode. A start/stop switch 42 is operable for alternately supplying, to the CPU 28, an ON signal to start the BP monitor and an OFF signal to stop the same, each time the switch 42 is operated.

Figure 2:
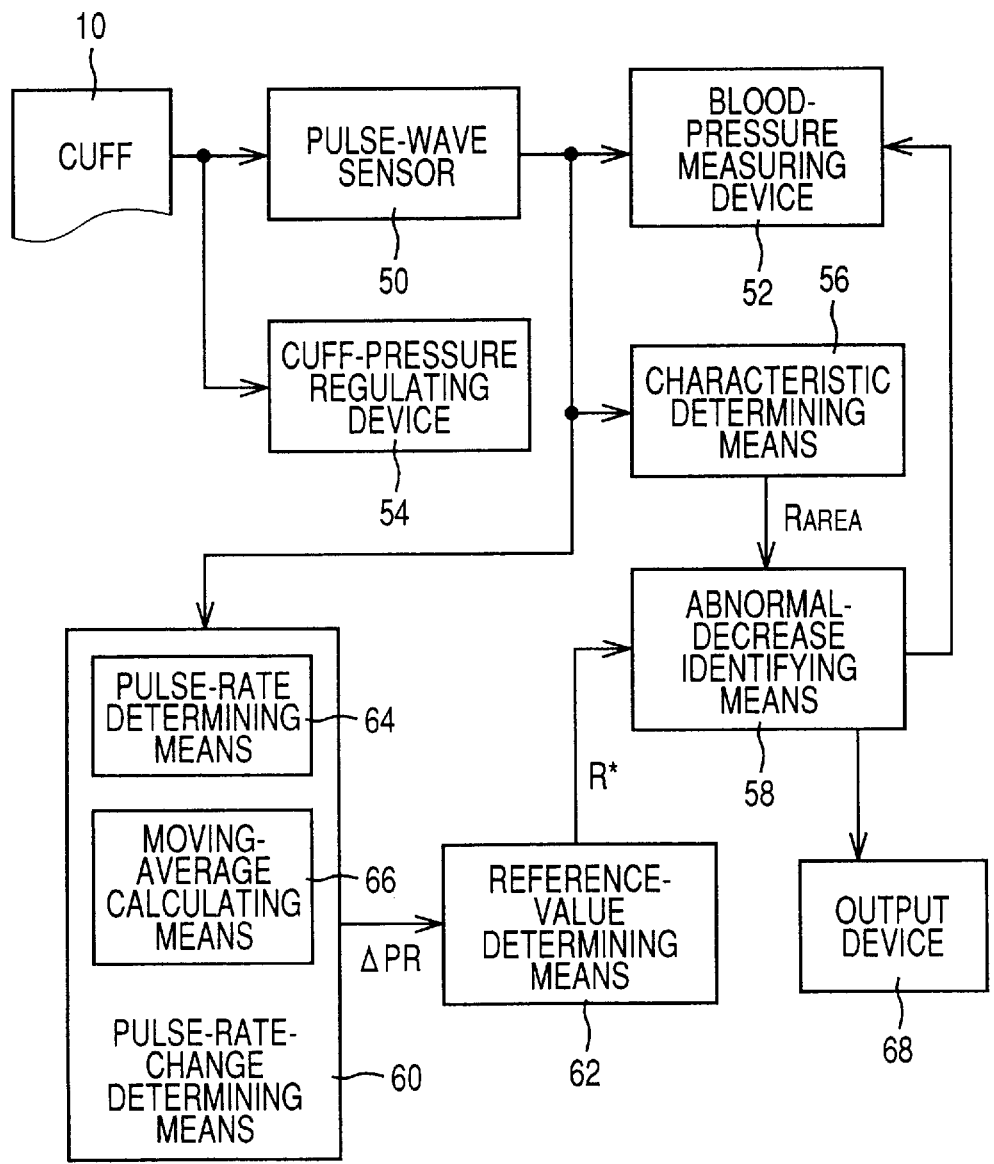
FIG. 2 is a block diagram for illustrating various functions of a control device of the apparatus of FIG. 1.

FIG. 2 illustrates various functions of the control device 26 of the present BP monitor. The BP monitor includes a pulse-wave sensor 50 which detects a pulse wave including heartbeat-synchronous pulses that are pressure oscillations produced in the cuff 10 in synchronism with subject's heartbeats when the cuff pressure $P_c$ is changed. The BP monitor also includes a blood-pressure (BP) measuring device 52 which determines, according to a known oscillometric method, two cuff pressures at which the rate of change of pulse amplitudes $A_m$ obtained during the changing of the cuff pressure $P_c$ becomes maximal, as a systolic ($P_{SYS}$) and a diastolic ($P_{DIA}$) blood pressure of the subject, and determines a cuff pressure at which the greatest pulse amplitude is obtained, as a mean ($P_{MEAN}$) blood pressure of the subject. The BP measuring device 52 carries out a BP measurement not only when the start/stop switch 42 is operated to start the BP monitor, but also when an abnormal-decrease identifying means 58 identifies an abnormal decrease of the blood pressure of the subject, in a manner described later, with the mode switch 40 being placed in the BP-monitor mode.

Figure 6:
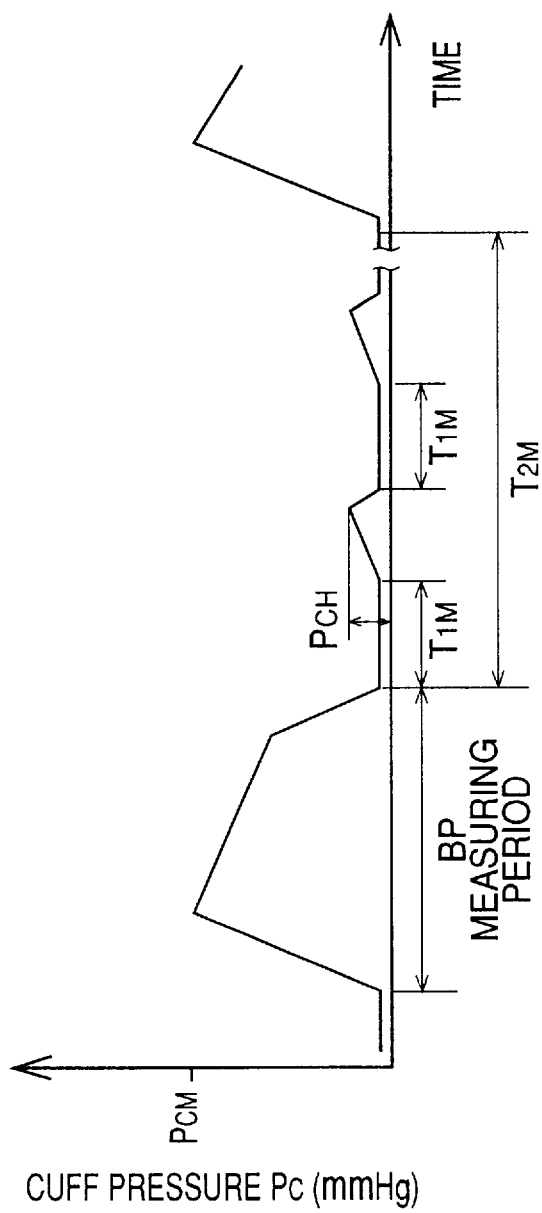
FIG. 6 is a time chart showing the time-wise change of cuff pressure $P_c$ regulated by the apparatus of FIG. 1.

As shown in FIG. 6, in each BP-measuring period of the BP measuring device 52, a cuff-pressure regulating device 54 quickly increases the cuff pressure $P_c$ up to a first target value, $P_{CM}$, which is pre-determined to be higher than a systolic BP value of the subject, and subsequently slowly decreases the cuff pressure $P_c$ at the rate of 2 to 3 mmHg/sec. In each non-BP-measuring period, $T_{2M}$, in which the BP measuring device 52 does not work, the cuff-pressure regulating device 54 iteratively increases and decreases the cuff pressure $P_c$ to and from a second target value, $P_{CH}$, which is pre-determined to be lower than a mean BP value of the subject, while inserting a predetermined rest period, $T_{1M}$, between successive two cuff-pressure regulating periods.

The control device 26 functions as a characteristic determining means 56 which determines a characteristic value relating to an envelope, H, (FIG. 7) of the pulse amplitudes A$_m$ detected by the pulse-wave sensor 50 during each of the iterative cuff-pressure changing periods of the cuff-pressure regulating device 54 within a predetermined range whose upper limit is lower than a mean BP value of the subject. For example, the characteristic determining means 56 determines the characteristic value of the envelope H based on an area, indicated at inclined lines in FIG. 7, which is defined by (i) the envelope H of the pulse amplitudes A$_m$ and (ii) a base line connecting the cuff-pressure values P$_C$ corresponding to the pulse amplitudes A$_m$, respectively, i.e., axis of abscissa indicative of the cuff pressure P$_c$ in the graph of FIG. 7. More specifically described, the characteristic determining means 56 determines, as the characteristic value of the envelope H, a ratio, R$_{AREA}$, of the area to a pulse amplitude corresponding to a lower limit of the predetermined range.

The control device 26 also functions as an abnormal-decrease identifying means 58 which identifies an abnormal decrease of the blood pressure of the subject based on the characteristic value determined by the characteristic determining means 56. The control device 26 further functions as a pulse-rate-change determining means 60 which determines a change, Δ PR, of a current pulse-rate value, PR$_n$, determined by a pulse-rate determining means 64, from a prior pulse-rate value, PR$_{n-1}$, determined by the pulse-rate determining means 64 or a moving average, PR$_{ave}$(=(PR$_{n-1}$+ . . . +PR$_{n-m}$)/m ), of a predetermined number, m, of prior pulse-rate values determined by the pulse-rate determining means 64 before the current pulse-rate value PR$_n$ is determined. The pulse-rate determining means 64 determines the pulse rate PR$_n$ based on a time interval between two successive heartbeat-synchronous pulses of the pulse-wave signal SM$_1$ which is detected by the pulse-wave sensor 50 each time the cuff pressure P$_c$ is increased to, or decreased from, the second target value P$_{CH}$ lower than the mean BP value of the subject by the cuff-pressure regulating device 54 during the non-BP-measuring period T$_{2M}$. The pulse-rate-change determining means 60 includes the pulse-rate determining means 64, and a moving-average determining means for determining the above-indicated moving average PR$_{ave}$.

Figure 8:
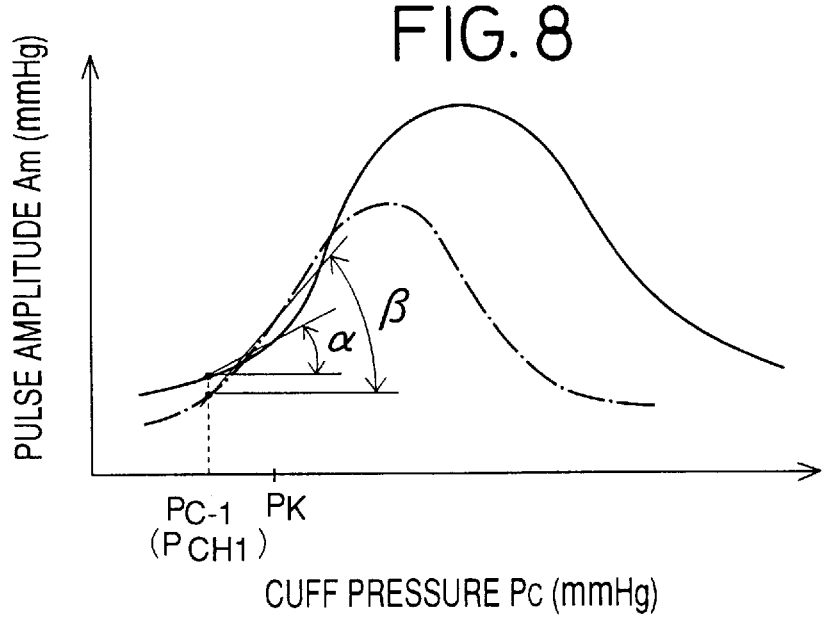
FIG. 8 is a graph for illustrating the manner in which the envelope of pulse amplitudes detected from an inflatable cuff is changed because of a decrease of the blood pressure of a living subject.

In the case where the blood pressure of the subject is normal, the envelope (indicated at solid line in FIG. 8) of the pulse amplitudes A$_m$ obtained when the cuff pressure P$_c$ is changed under the mean BP value of the patient, exhibits a small angle, α. On the other hand, when the blood pressure of the subject decreases, the upper-peak point of the envelope (indicated at one-dot chain line) of the pulse amplitudes A$_m$ obtained under the same conditions, decreases and moves left in FIG. 8, therefore exhibits a greater angle, β. Accordingly, in the latter case, the ratio R$_{AREA}$ increases. The present invention has been developed based on this finding. For example, the abnormal-decrease identifying means 58 identifies an abnormal decrease of the blood pressure of the subject, when a ratio R$_{AREA}$ determined by the characteristic determining means 56 exceeds a reference value R*. The BP monitor includes an output device 68 which outputs information indicating that the abnormal-decrease identifying means 58 has identified an abnormal decrease of the blood pressure of the subject.

The reference value R* may be a predetermined constant value. However, in the present embodiment, the control device 26 functions as a reference-value determining means 62 which determines a reference value R* based on the pulse-rate change ΔPR determined by the pulse-rate-change determining means 60, according to the following predetermined expression (1) pre-stored in the ROM 32 and illustrated in FIG. 5:

$$R^* = k_1 \times \Delta PR + k_2 \quad (1)$$

where k$_1$ and k$_2$ are a first and a second constant, respectively.

Next, there will be described the operation of the control device 26 of the BP monitor by reference to the flow charts of FIGS. 3 and 4 which represent the control program pre-stored in the ROM 32.

Figure 3:
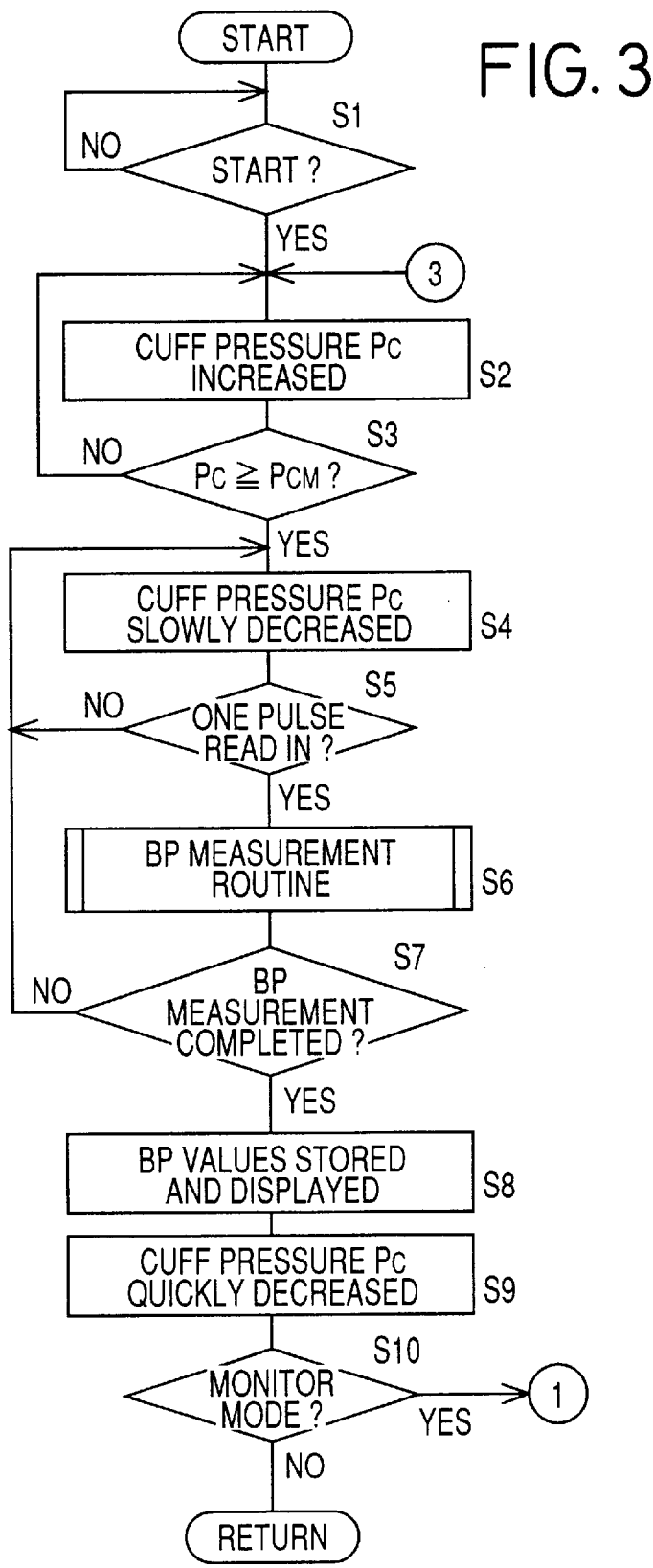
FIG. 3 is a flow chart representing a portion of a control program according to which the control device of the apparatus of FIG. 1 functions as illustrated in FIG. 2.

First, at Step S1 of FIG. 3, the CPU 28 of the control device 26 judges whether the start/stop switch 42 has been operated to start the present BP monitor, based on the signal supplied from the switch 42. If a negative judgment is made at Step S1, Step S1 is repeated. Meanwhile, a positive judgment is made at Step S1, the control of the CPU 28 proceeds with Step S2 to operate the air pump 14 and the pressure regulator valve 16 to increase quickly the pressure P$_c$ of the cuff 10.

Figure 7:
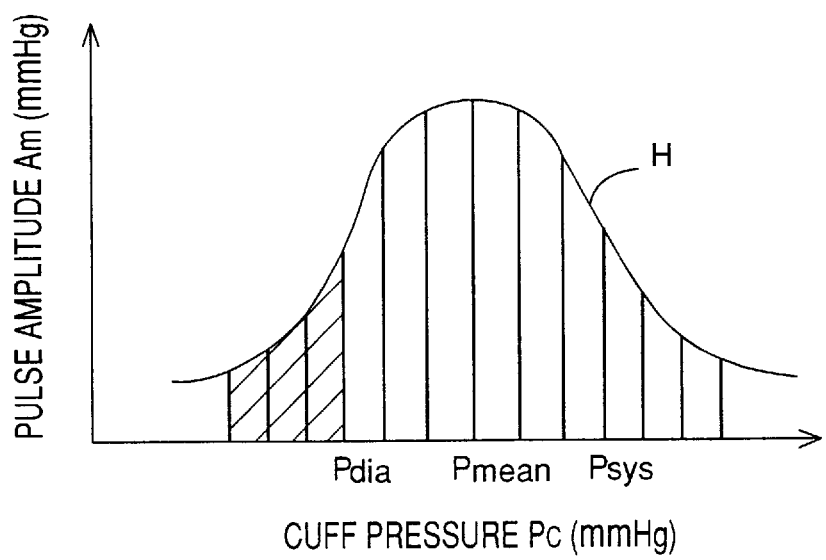
FIG. 7 is a graph for illustrating an area calculated by the apparatus of FIG. 1 at a step of the control program represented by the flow chart of FIG. 4.

Step S2 is followed by Step S3 to judge whether the cuff pressure P$_c$ has been increased up to a first predetermined target value PCM, e.g., 180 mmHg. If a negative judgment is made at Step S3, Steps S2 and S3 are repeated. Meanwhile, if a positive judgment is made at Step S3, the control of the CPU 28 proceeds with Step S4 to stop the air pump 14 and change the degree of opening of the regulator valve 16 to start decreasing the cuff pressure P$_c$ at the low rate of 2 to 3 mmHg/sec suitable for blood pressure measurements. Step S4 is followed by Step S5 to judge whether the CPU 28 has read in one heartbeat-synchronous pulse of the pulse-wave signal SM$_1$ from the band-pass filter 22. If a negative judgment is made at Step S5, Steps S4 and S5 are repeated. Meanwhile, if a positive judgment is made at Step S5, the control of the CPU 28 goes to Step S6, i.e., oscillometric BP-value determining routine. As shown in FIG. 7, a cuff pressure at which the pulse amplitudes A$_m$ largely increase during the slow decreasing of the cuff pressure P$_c$, is determined as a systolic blood pressure P$_{SYS}$ of the subject; a cuff pressure at which the pulse amplitudes A$_m$ largely decrease is determined as a diastolic blood pressure P$_{DIA}$ of the subject; and a cuff pressure at which the greatest pulse amplitude is detected is determined as a mean blood pressure P$_{MEAN}$ of the subject. Step S6 is followed by Step S7 to judge whether the BP-value determination at Step S6 has been completed. If a negative judgment is made at Step S7, Steps S4 to S7 are repeated. Meanwhile, if a positive judgment is made at Step S7, the control of the CPU 28 goes to Step S8 to store the determined BP values P$_{SYS}$, P$_{MEAN}$, P$_{DIA}$ in the RAM 30 and command the display 38 to display numerals indicative of the determined BP values P$_{SYS}$, P$_{MEAN}$, P$_{DIA}$. Step S8 is followed by Step S9 to decrease quickly the cuff pressure P$_c$, thereby releasing the subject's arm from the pressing of the cuff 10. In the present embodiment, Steps S2 to S9 correspond to the BP measuring device 52.

At Step S10, the CPU 28 judges whether the mode switch 40 indicates that the BP-monitor mode has been selected, based on the signal supplied from the switch 40. A negative judgment made at Step S10 indicates that the present BP monitor is now in the single-measurement mode. In this case, the control of the CPU 28 returns to Step S1. On the other hand, a positive judgment made at Step S10 indicates that the present BP monitor is now in the BP-monitor mode. In the latter case, the control of the CPU 28 goes to Step S11 and the following steps, i.e., BP monitoring routine.

At Step S11, a second timer or counter, T$_2$, is reset to zero and, at Step S12, a first timer or counter, T$_1$, is reset to zero. At Step S13, one is added to each of the respective contents of the first and second timers T$_1$, T$_2$ and, at Step S14, the CPU 28 judges whether the content or time counted or measured by the first timer $T_1$ has increased up to a first predetermined reference value, $T_{1M}$, of, e.g., 1 to 5 minutes. The first reference value $T_{1M}$ corresponds to a time interval between successive two cuff-pressure regulating periods in each of which the cuff pressure $P_c$ is increased up to a second predetermined target value $P_{CH}$ of, e.g., 60 mmHg during a second predetermined time interval, $T_{2M}$, between two successive BP-measuring periods, as illustrated in FIG. 6.

Initially, negative judgments are made at Step S14, and Steps S13 and S14 are repeated. Meanwhile, if a positive judgment is made at Step S14, the control of the CPU 28 goes to Step S15 to operate the air pump 14 and the pressure regulator valve 16 to increase the cuff pressure $P_c$ at a predetermined low rate. This low rate is predetermined such that four or more heartbeat-synchronous pulses of the pulse-wave signal $SM_1$ are obtained through the band-pass filter 22 while the cuff pressure $P_c$ is increased from atmospheric pressure up to the second target value $P_{CH}$. The low rate is, e.g., 10 mmHg/sec. At Step S16, the CPU 28 reads in each heartbeat-synchronous pulse of the signal $SM_1$, determines the amplitude $A_m$ of each pulse, the time when that pulse is read in, and the cuff pressure $P_c$ at the time of reading of that pulse, and store the thus obtained data in the RAM 30.

Step S16 is followed by Step S17 to judge whether the cuff pressure $P_c$ has been increased up to the second target value $P_{CH}$. The second target value $P_{CH}$ is predetermined to be sufficiently lower than a mean BP value of the subject, and allows the CPU 28 or the control device 26 to identify a significant change of the pulse amplitudes $A_m$. As described above, the target value $P_{CH}$ may be 60 mmHg. If a negative judgment is made at Step S17, Steps S15, S16, and S17 are repeated. Meanwhile, if a positive judgment is made at Step S17, the control of the CPU 28 goes to Step S18 to stop the low-rate increasing of the cuff pressure $P_c$ and cause the cuff pressure $P_c$ to be quickly decreased down to atmospheric pressure.

Step S18 is followed by Step S19 to produce, based on the pulse amplitudes $A_m$ and the cuff pressures $P_c$ determined and stored at Step S16, an envelope H of the pulse amplitudes $A_m$ in a two-dimensional coordinate system defined by an axis of abscissa indicative of the cuff pressure $P_c$ (mmHg) and an axis of ordinate indicative of the pulse amplitude $A_m$ (mmHg), as illustrated in FIG. 7. The axis of abscissa corresponds to a base line which connects the cuff pressures $P_c$ corresponding to the pulse amplitudes $A_m$, respectively. Subsequently, the CPU 28 determines an area, S, defined or bounded by the envelope H and the base line, within a predetermined pressure range between, e.g., 30 mmHg and 60 mmHg. The area S may be calculated by integration. In the present embodiment, however, the area S is obtained by approximation. For example, in the case where the CPU 28 obtains, at Step S16, a pulse amplitude, $A_{m30}$, corresponding to a cuff pressure $P_c$ of 30 mmHg, a pulse amplitude, $A_{m40}$, corresponding to a cuff pressure $P_c$ of 40 mmHg, a pulse amplitude, $A_{m50}$, corresponding to a cuff pressure $P_c$ of 50 mmHg, and a pulse amplitude, $A_{m60}$, corresponding to a cuff pressure $P_c$ of 60 mmHg, when the cuff pressure $P_c$ is increased from atmospheric pressure up to the target value $P_{CH}$ of 60 mmHg at Step S15, the CPU 28 approximates the area S by the sum of the four amplitudes, i.e., $S = A_{m30} + A_{m40} + A_{m50} + A_{m60}$. Finally, the CPU 28 determines a characteristic, $R_{AREA}$, of the envelope H by the following expression (2):

$$R_{AREA} = (A_{m30} + A_{m40} + A_{m50} + A_{m60})/A_{m30} \qquad (2)$$

Thus, Step S19 corresponds to the characteristic determining means 56.

Step S19 is followed by Step S20 to determine a current pulse rate, $PR_n$, from a time interval between the respective times of occurrence of two successive heartbeat-synchronous pulses of the pulse-wave signal $SM_1$ determined and stored at Step S16. Step S20 corresponds to the pulse-rate determining means 64. Step S20 is followed by Step S21 to calculate a moving average, $PR_{ave}$ (=$(PR_{n-1} + PR_{n-2} + \ldots + PR_{n-m})/m$), of a predetermined number, m, of prior pulse rates, $PR_{n-1}, PR_{n-2}, \ldots, PR_{n-m}$, determined at Step S19 in the same number m of prior control cycles before the current control cycle. Step S21 corresponds to the moving-average calculating means 66. Step S21 is followed by Step S22 to determine a change, $\Delta PR$ (=$PR_n - PR_{ave}$), of the current pulse rate $PR_n$ determined at Step 20 from the moving average $PR_{ave}$ determined at Step S21. Step S22 corresponds to the pulse-rate-change determining means 60.

Figure 5:
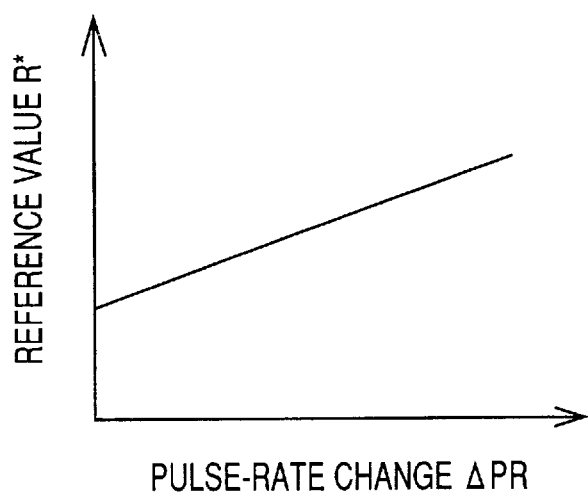
FIG. 5 is a graph representing a relationship used by the apparatus of FIG. 1 at a step of the control program represented by the flow chart of FIG. 4.

Subsequently, the control of the CPU 28 goes to Step S23 to determine a reference value R* based on the pulse-rate change $\Delta PR$ determined at Step S22, according to the pre-stored expression (1), i.e., relationship shown in FIG. 5. Step S23 corresponds to the reference-value determining means 62. The research of the Applicant has found that as the blood pressure P of a living subject decreases, the characteristic $R_{AREA}$ of the subject increases and the pulse rate PR decreases. Based on this finding, the reference value R* is modified depending upon the pulse-rate change $\Delta PR$. Thus, the accuracy of identification of an abnormal BP decrease of the subject is improved.

Step S23 is followed by Step S24 to judge whether the characteristic value $R_{AREA}$ determined at Step S19 is greater than the reference value R* determined at Step S23. Step S24 corresponds to the abnormal-decrease identifying means 58. If a positive judgment is made at Step S24, the control of the CPU 28 goes to Step S25 to operate the display 38 to output a message to inform the operator of the identification of the abnormal BP decrease of the subject, and subsequently to Step S2 and the following steps corresponding to part of the BP measuring device 52 to measure a BP value or values of the subject immediately after the identification of the abnormal BP decrease.

On the other hand, if a negative judgment is made at Step S24, the control of the CPU 28 goes to Step S26 to decrease the cuff pressure $P_c$ down to atmospheric pressure and subsequently to Step S27 to judge whether the content or time counted or measured by the second timer $T_2$ has increased up to a second predetermined reference value $T_{2M}$ of, e.g., 10 to 30 minutes. The second reference value $T_{2M}$ corresponds the time interval between two BP-measuring periods, as shown in FIG. 6. Thus, the BP measuring device 52 periodically carries out a BP measuring operation at Steps S2 through S9. Initially, negative judgments are made at Step S27, and Steps S12 and the following steps are repeated. Meanwhile, if a positive judgment is made at Step S27, the control of the CPU 28 goes back to Step S2 and the following steps.

Figure 4:
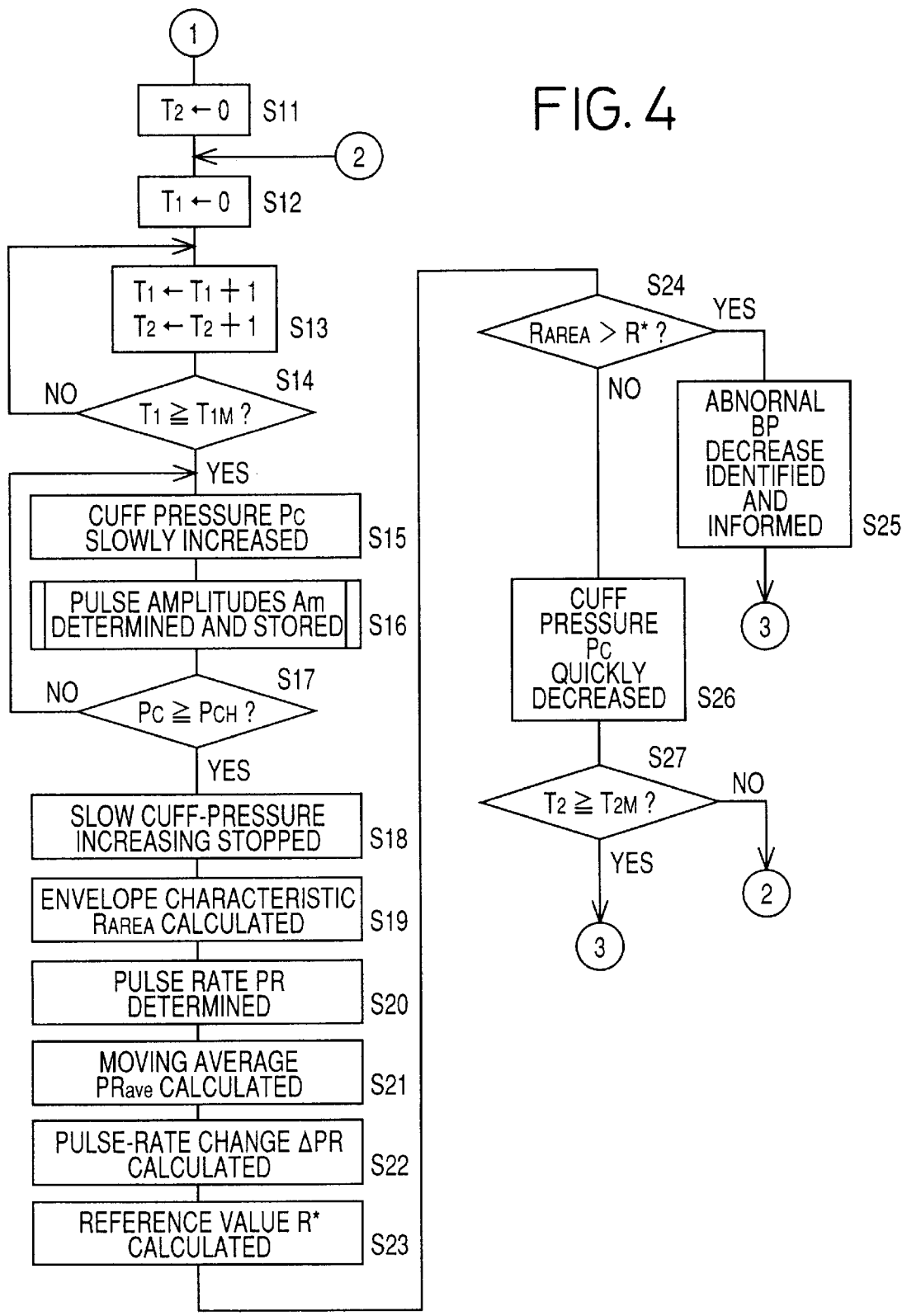
FIG. 4 is a flow chart representing another portion of the control program according to which the control device of the apparatus of FIG. 1 functions as illustrated in FIG. 2.

Thus, according to the flow charts of FIGS. 3 and 4, the cuff pressure $P_c$ is changed as time elapses, as shown in FIG. 6. That is, after the initial BP-measuring operation is carried out in response to the operation of the start/stop switch 42 and the first time interval $T_{1M}$ elapses, the cuff pressure $P_c$ is periodically increased up to the second target pressure $P_{CH}$ lower than a mean BP value of the subject, during the non-BP-measuring period, i.e., BP-monitoring period. The control device 26 of the present BP monitor determines a characteristic value $R_{AREA}$ based on the pulse amplitudes $A_m$ and the corresponding cuff pressures $P_c$ that are obtained during each cuff-pressure regulating period, and identifies a possible abnormal BP decrease of the subject based on the thus determined characteristic value $R_{AREA}$.

As is apparent from the foregoing description relating to the first embodiment of the present invention, each time the air pump 14 and the pressure regulator valve 16 are operated to increase the cuff pressure $P_c$ to the second target pressure $P_{CH}$ lower than a mean BP value of a living subject, the CPU 28 calculates the characteristic value $R_{AREA}$ at Step S29, and identifies an abnormal BP decrease of the subject based on the determined characteristic value $R_{AREA}$ at Step S24. Thus, the present BP monitor monitors, with high accuracy, the blood pressure of the subject by utilizing the finding that the slope of the envelope H of the pulse amplitudes $A_m$ detected while the cuff pressure $P_C$ is changed within the predetermined range whose upper limit is lower than the mean BP value of the subject changes when the blood pressure of the subject changes. In addition, since the slope of the envelope H is obtained when the cuff pressure $P_c$ is changed under the mean BP value of the subject, the subject does not feel discomfort due to the pressing of the cuff 10.

Also, in the present embodiment, if an abnormal BP decrease of the subject is identified at Step S24, the BP measuring device 52 automatically carries out a BP measuring operation according to a series of predetermined steps. Thus, an actual BP value or values of the subject at the time of identification of the abnormal BP decrease is promptly measured by the BP measuring device 52. Therefore, a medical staff such as a doctor or a nurse can quickly take an appropriate action for the subject.

Moreover, at Step S23, the CPU 28 determines, according to the pre-stored expression (1), the reference value R* based on the pulse-rate change Δ PR of the current pulse rate $PR_n$ that is determined based on the same pulse-wave signal $SM_1$ as that used to determine the characteristic value $R_{AREA}$ and, at Step S24, the CPU 28 identifies an abnormal BP decrease of the subject if the characteristic value $R_{AREA}$ is greater than the reference value R*. For example, in the case where the blood pressure of a patient abnormally decreases because of falling in shock, the envelope H of pulse amplitudes $A_m$ detected from the patient in shock becomes flat or level. In this case, therefore, it is not easy to identify the shock of the patient based on only the slope of the pulse amplitudes $A_m$ with respect to the cuff pressure $P_c$. In the present embodiment, however, the reference value R* is determined depending upon the pulse-rate change Δ PR that decreases as the blood pressure of the patient decreases. Thus, the blood pressure of the patient, i.e., the characteristic value $R_{AREA}$ is monitored in association with the pulse rate PR of the patient, i.e., the reference value R*. Accordingly, the present BP monitor can immediately identify, with high accuracy, that the patient has fallen in shock.

Figure 9:
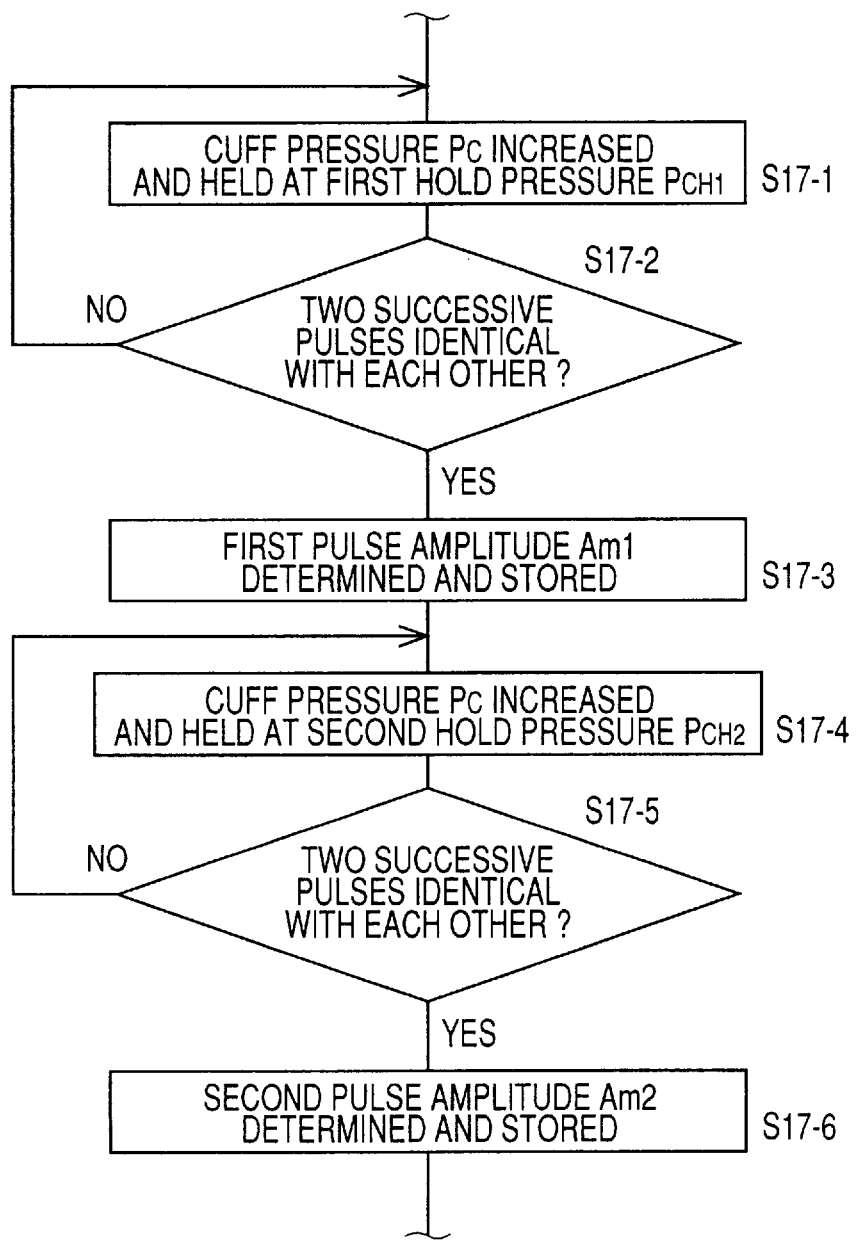
FIG. 9 is a flow chart corresponding to FIG. 4, representing a portion of a control program according to which a control device of another BP monitor apparatus as a second embodiment of the invention functions.
Figure 10:
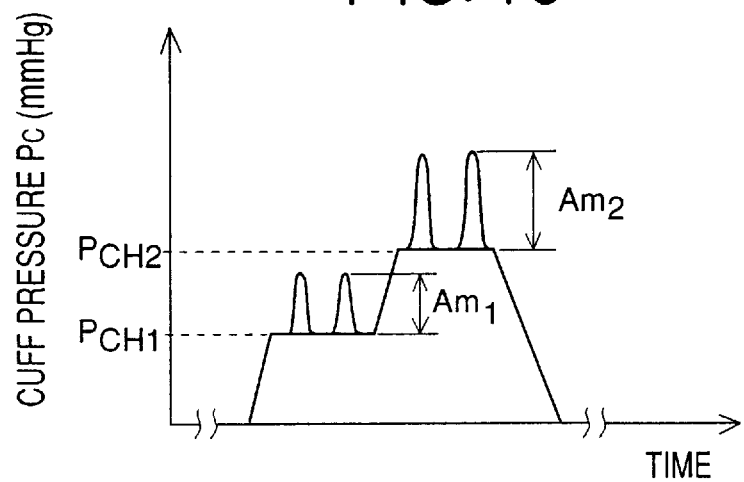
FIG. 10 is a time chart showing the time-wise change of cuff pressure $P_c$ regulated by the apparatus of FIG. 9.

Next, there will be described a second embodiment of the present invention by reference to FIGS. 9 and 10. The second embodiment relates to a BP monitor which has the same hardware construction as that of the first embodiment shown in FIG. 1 and which operates according to the control program represented by the flow charts of FIGS. 3 and 4 except that in the second embodiment, Steps S17-1 to S17-6 of FIG. 9 replace Steps S15, S16, and S17 of FIG. 4. The same reference numerals as used in the first embodiment are used to designate the corresponding elements or parts of the second embodiment and the description thereof is omitted.

In the second embodiment, a control device 26 of the BP monitor functions as part of a blood pressure regulating device 54 which increases a cuff pressure $P_c$ up to a first predetermined hold value, $P_{CH1}$, and holds the cuff pressure $P_c$ at the first hold value $P_{CH1}$ for a predetermined duration, and subsequently increases the cuff pressure $P_c$ up to a second predetermined hold value, $P_{CH2}$, higher than the first hold value $P_{CH1}$ and holds the cuff pressure $P_c$ at the second hold value $P_{CH1}$ for the same duration. The control device 26 also functions as a characteristic determining means 56 which determines a characteristic, $R_{ENV}$, relating to an envelope of two pulse amplitudes $A_{m1}$, $A_{m2}$ which are detected when the cuff pressure $P_c$ is held at the first and second hold values $P_{CH1}$, $P_{CH2}$, respectively.

In the present embodiment, after a positive judgment is made at Step S14, the control of a CPU 28 of the control device 26 goes to Step S17-1 to increase the cuff pressure $P_c$ up to a first predetermined hold value $P_{CH1}$ and holds the cuff pressure $P_c$ at the first hold value $P_{CH1}$ for a predetermined duration. The first hold value $P_{CH1}$ is, e.g., 30 mmHg. Subsequently, at Step S17-2, the CPU 28 judges whether two successive heartbeat-synchronous pulses detected with the cuff pressure $P_c$ being held at the first hold value $P_{CH1}$ have an identical amplitude. This step is provided for avoiding reading noise as a heartbeat-synchronous pulse. Since a band-pass filter 22 of the present BP monitor provides pulses when the cuff pressure $P_c$ is held at a certain value, i.e., the first hold value $P_{CH1}$ at Step S17-1 (or a second hold value $P_{CH2}$ at Step S17-4), those pulses have a more accurate waveform than the pulses provided by the band-pass filter 22 in the first embodiment while the cuff pressure $P_c$ is changed. If a negative judgment is made at Step S17-2, Steps S17-1 and S17-2 are repeated. On the other hand, if a positive judgment is made at Step S17-2, the control of the CPU 28 goes to Step S17-3 to store the identical amplitude of the two pulses as a first pulse amplitude $A_{m1}$ in a RAM 30.

Step S17-3 is followed by Step S17-4 to increase the cuff pressure $P_c$ up to a second predetermined hold value $P_{CH2}$ and holds the cuff pressure $P_c$ at the second hold value $P_{CH2}$ for the same duration. The second hold value $P_{CH2}$ is, e.g., 60 mmHg. The second hold value $P_{CH2}$ is so pre-determined as to obtain a greater pulse amplitude than that obtained at the first hold pressure $P_{CH1}$. Subsequently, at Step S17-5, the CPU 28 judges whether two successive heartbeat-synchronous pulses detected with the cuff pressure $P_c$ being held at the second hold value $P_{CH2}$ have an identical amplitude. If a negative judgment is made at Step S17-5, Steps S17-4 and S17-5 are repeated. On the other hand, if a positive judgment is made at Step S17-5, the control of the CPU 28 goes to Step S17-6 to store the identical amplitude of the two pulses as a second pulse amplitude $A_{m2}$ in the RAM 30. The cuff pressure $P_c$ is changed as time elapses, as illustrated in FIG. 10.

After the cuff pressure $P_c$ is decreased down to atmospheric pressure at Step S18, the control of the CPU 28 goes to Step S19 to determine a characteristic value, $R_{ENV}$, of the envelope of the two pulse amplitudes $A_{m1}$, $A_{m2}$ determined and stored at Steps S17-3 and S17-6, according to the following expression (3):

$$R_{ENV} = A_{m2}/A_{m1} \tag{3}$$

The BP monitor as the second embodiment enjoys the same advantages as those of the BP monitor as the first embodiment. In addition, the characteristic value $R_{ENV}$ is easily calculated from the two pulse amplitudes $A_{m1}$, $A_{m2}$.

Moreover, noise is effectively removed from the pulse-wave signal $SM_1$ supplied from the band-pass filter 22, because the cuff pressure $P_c$ is held at the first or second hold pressure $P_{CH1}$, $P_{CH2}$ until two successive pulses having an identical amplitude are detected.

Furthermore, since pulses are detected when the cuff pressure $P_c$ is held at the first or second hold pressure $P_{CH1}$, $P_{CH2}$, those pulses enjoy an accurate waveform free from distortion due to the changing of the cuff pressure $P_c$ and accordingly provide an accurate amplitude $A_{m1}$, $A_{m2}$. Therefore, the characteristic value $R_{ENV}$ is determined with accuracy, and the blood pressure of the subject is monitored with reliability.

While the present invention has been described in its preferred embodiments, the present invention may otherwise be embodied.

While in each of the first and second embodiments the control device 28 determines the characteristic value $R_{AREA}$, $R_{ENV}$ based on the pulse amplitudes $A_m$, $A_{m1}$, $A_{m2}$ detected when the cuff-pressure regulating device 54 increases the cuff pressure $P_c$ within the predetermined pressure range whose lower and upper limits are 30 and 60 mmHg, respectively, it is possible to determine a characteristic value $R_{AREA}$, $R_{ENV}$ based on pulse amplitudes $A_m$, $A_{m1}$, $A_{m2}$ detected when the cuff pressure $P_c$ is decreased within a predetermined pressure range.

Although in the first and second embodiments the control device 26 determines the characteristic value $R_{AREA}$, $R_{ENV}$ according to the expression (2) or (3), it is possible to determine, as a characteristic of the envelope H of pulse amplitudes, an area defined by the envelope of normalized pulse amplitudes $A_{m1}$, or a difference between the two pulse amplitudes $A_{m1}$, $A_{m2}$. The normalization of the pulse amplitudes $A_m$ is effected by regarding, as one, the greatest one of the pulse amplitudes $A_m$.

While in the first and second embodiments the second target pressure $P_{CH}$ or the second hold pressure $P_{CH2}$ is 60 mmHg, it is possible to employ, as the second target or hold pressure $P_{CH}$, $P_{CH2}$, a different pressure which is lower than a mean BP value of a living subject.

However, it is more preferable to employ, as the second target or hold pressure $P_{CH}$, $P_{CH2}$, a pressure lower than a diastolic BP value of a living subject, because the low pressure does not stop the blood flow through the arteries under the cuff 10.

While in each of the first and second embodiments the control device 26 determines, at Step S20, the pulse rate PR of the subject based on the pulse wave (i.e., signal $SM_1$) which is the pressure oscillation produced in the cuff 10 employed for the blood pressure measurements, it is possible to employ a different sort of pulse-wave sensor which detects a different sort of pulse wave, such as a photoelectric pulse wave, a volumetric pulse wave, an impedance pulse wave, or an electrocardiograph which produces an electrocardiogram signal, and determine a pulse rate based on the different pulse wave or signal.

It is to be understood that the present invention may be embodied with other changes, improvements, and modifications that may occur to those skilled in the art without departing from the spirit and scope of the invention defined in the appended claims.

What is claimed is:

1. A blood pressure monitor apparatus for monitoring a blood pressure of a living subject, by changing a pressing pressure of an inflatable cuff being wound around a body portion of a living subject, comprising:

a cuff-pressure regulating device which iteratively changes the pressure of said cuff within a predetermined range whose upper limit is lower than a diastolic blood pressure of the subject;

a pulse-wave sensor which detects an amplitude of each of a plurality of heartbeat-synchronous pulses of a pulse wave which is produced in said cuff when said pressure of the cuff is changed within said predetermined range by said regulating device;

characteristic determining means for determining a characteristic value relating to an envelope of the pulse amplitudes detected by said pulse-wave sensor during each of the iterative changes of the pressure of said cuff by said regulating device within said predetermined range; and identifying means for identifying an abnormal decrease of said blood pressure of the subject based on the characteristic value determined by said characteristic determining means.

2. A blood pressure monitor apparatus according to claim 1, wherein said characteristic determining means comprises area-using characteristic determining means for determining said characteristic value based on an area defined by said envelope of said pulse amplitudes and a base line connecting a plurality of cuff pressures corresponding to said pulse amplitudes, respectively.

3. A blood pressure monitor apparatus according to claim 2, wherein said area-using characteristic determining means comprises means for determining, as said characteristic value, a ratio of said area to the pulse amplitude corresponding to a lower limit of said predetermined range.

4. A blood pressure monitor apparatus according to claim 2, wherein said area-using characteristic determining means comprises means for determining, as said characteristic value, an area defined by said base line and an envelope of respective normalized values of said pulse amplitudes.

5. A blood pressure monitor apparatus according to claim 1, wherein said characteristic determining means comprises amplitude-using characteristic determining means for determining said characteristic value based on at least two of said pulse amplitudes.

6. A blood pressure monitor apparatus according to claim 5, wherein said amplitude-using characteristic determining means comprises means for determining, as said characteristic value, a ratio of the pulse amplitude corresponding to said upper limit of said predetermined range to the pulse amplitude corresponding to a lower limit of the predetermined range.

7. A blood pressure monitor apparatus according to claim 5, wherein said amplitude-using characteristic determining means comprises means for determining, as said characteristic value, a difference between the pulse amplitude corresponding to said upper limit of said predetermined range and the pulse amplitude corresponding to a lower limit of the predetermined range.

8. A blood pressure monitor apparatus according to claim 1, further comprising a blood pressure measuring device which automatically carries out, when said identifying means identifies said abnormal decrease of said blood pressure of the subject, a blood pressure measurement on the subject according to a series of predetermined steps.

9. A blood pressure monitor apparatus according to claim 1, further comprising a pulse-rate sensor which detects a pulse rate of the subject when said pressure of the cuff is changed within said predetermined range by said regulating device.

10. A blood pressure monitor apparatus according to claim 9, wherein said pulse-rate sensor comprises pulse-rate determining means for determining said pulse rate based on at least two pulses of said heartbeat-synchronous pulses of said pulse wave detected by said pulse-wave sensor from said cuff when said pressure of the cuff is changed within said predetermined range by said regulating device.

11. A blood pressure monitor apparatus according to claim 9, further comprising pulse-rate-change determining means for determining a change of a current pulse-rate value detected by said pulse-rate sensor, from at least one prior pulse-rate value detected by said pulse-rate sensor before said current pulse-rate value is detected.

12. A blood pressure monitor apparatus according to claim 11, wherein said pulse-rate-change determining means comprises means for determining said change of said current pulse-rate value from a moving average of a plurality of prior pulse-rate values detected by said pulse-rate sensor before said current pulse-rate value is detected.

13. A blood pressure monitor apparatus according to claim 11, further comprising reference-value determining means for determining a reference value, R*, based on the pulse-rate change, $\Delta$ PR, determined by said pulse-rate-change determining means, according to a following predetermined expression:

$$R^* = k_1 \times \Delta PR + k_2$$

where $k_1$ and $k_2$ are a first and a second constant, respectively, wherein said identifying means identifies said abnormal decrease of said blood pressure of the subject when said characteristic value determined by said characteristic determining means is greater than said reference value R*.

14. A blood pressure monitor apparatus according to claim 13, further comprising a memory which stores data indicative of said predetermined expression.

15. A blood pressure monitor apparatus according to claim 1, wherein said cuff-pressure regulating device comprises means for changing the pressure of said cuff to a predetermined first hold value equal to a lower limit of said predetermined range and holding the cuff pressure at said first hold value and changing said cuff pressure to a predetermined second hold value higher than said first hold value and equal to said upper limit of the predetermined range and holding said cuff pressure at said second hold value, and wherein said characteristic determining means determines said characteristic value based on the pulse amplitude detected by said pulse-wave sensor when said cuff pressure is held at said first hold value and the pulse amplitude detected by said pulse-wave sensor when said cuff pressure is held at said second hold value.

16. A blood pressure monitor apparatus according to claim 15, wherein said pulse-wave sensor comprises means for detecting an identical amplitude of two heartbeat-synchronous pulses of said pulse wave when the pressure of said cuff pressure is held at each of said first and second hold values, and wherein said characteristic determining means determines said characteristic value based on the identical pulse amplitude detected by said pulse-wave sensor when said cuff pressure is held at said first hold value and the identical pulse amplitude detected by said pulse-wave sensor when said cuff pressure is held at said second hold value.

17. A blood pressure monitor apparatus according to claim 1, further comprising a blood pressure measuring device which automatically carries out a blood pressure measurement on the subject at a predetermined period, wherein said cuff-pressure regulating device automatically changes the pressure of said cuff at a predetermined period which is shorter than the predetermined period of operation of said blood pressure measuring device.

18. A blood pressure monitor apparatus according to claim 1, further comprising an output device which outputs information indicating that said identifying means identifies said abnormal decrease of said blood pressure of the subject.

19. A blood pressure monitor apparatus for monitoring a blood pressure of a living subject, by changing a pressing pressure of an inflatable cuff being wound around a body portion of a living subject, comprising;

a cuff-pressure regulating device which iteratively changes the pressure of said cuff within a predetermined range whose upper limit is lower than a mean blood pressure of the subject;

a pulse-wave sensor which detects an amplitude of each of a plurality of heartbeat-synchronous pulses of a pulse wave which is produced in said cuff when said pressure of the cuff is changed within said predetermined range by said regulating device;

characteristic determining means for determining a characteristic value relating to an envelope of the pulse amplitudes detected by said pulse-wave sensor during each of the iterative changes of the pressure of said cuff by said regulating device within said predetermined range; and identifying means for identifying an abnormal decrease of said blood pressure of the subject based on the characteristic value determined by said characteristic determining means, wherein said characteristic determining means comprises area-using characteristic determining means for determining said characteristic value based on an area defined by said envelope of said pulse amplitudes and a base line connecting a plurality of cuff pressures corresponding to said pulse amplitudes, respectively.

20. A blood pressure monitor apparatus for monitoring a blood pressure of a living subject, by changing a pressing pressure of an inflatable cuff being wound around a body portion of a living subject, comprising:

a cuff-pressure regulating device which iteratively changes the pressure of said cuff within a predetermined range whose upper limit is lower than a mean blood pressure of the subject;

a pulse-wave sensor which detects an amplitude of each of a plurality of heartbeat-synchronous pulses of a pulse wave which is produced in said cuff when said pressure of the cuff is changed within said predetermined range by said regulating device;

characteristic determining means for determining a characteristic value relating to an envelope of the pulse amplitudes detected by said pulse-wave sensor during each of the iterative changes of the pressure of said cuff by said regulating device within said predetermined range; and identifying means for identifying an abnormal decrease of said blood pressure of the subject based on the characteristic value determined by said characteristic determining means, wherein said cuff-pressure regulating device comprises means for changing the pressure of said cuff to a predetermined first hold value equal to a lower limit of said predetermined range and holding the cuff pressure at said first hold value and changing said cuff pressure to a predetermined second hold value higher than said first hold value and equal to said upper limit of the predetermined range and holding said cuff pressure at said second hold value, and wherein said characteristic determining means determines said characteristic value based on the pulse amplitude detected by said pulse-wave sensor when said cuff pressure is held at said first hold value and the pulse amplitude detected by said pulse-wave sensor when said cuff pressure is held at said second hold value.

* * * * *